(12) United States Patent
Abbott

(10) Patent No.: US 6,255,357 B1
(45) Date of Patent: Jul. 3, 2001

(54) PRODUCTION OF METHANOL

(75) Inventor: Peter Edward James Abbott, Eaglescliffe (GB)

(73) Assignee: Imperial Chemical Industries PLC, London (GB)

(*) Notice: Subject to any disclaimer, the term of this patent is extended or adjusted under 35 U.S.C. 154(b) by 0 days.

(21) Appl. No.: 09/459,843

(22) Filed: Dec. 13, 1999

Related U.S. Application Data

(63) Continuation of application No. PCT/GB98/01670, filed on Jun. 8, 1998.

(30) Foreign Application Priority Data

Jun. 13, 1997 (GB) .................................................. 9712209

(51) Int. Cl.⁷ .................................................. C07C 27/00
(52) U.S. Cl. ..................... 518/700; 518/702; 518/704; 518/707
(58) Field of Search .................... 518/702, 704, 518/707, 700

(56) References Cited

U.S. PATENT DOCUMENTS

| | | |
|---|---|---|
| 4,239,693 | 12/1980 | McCallister . |
| 4,910,228 | 3/1990 | Lywood . |
| 5,177,114 | 1/1993 | Van Dijk et al. . |
| 5,300,275 * | 4/1994 | Lywood ................................ 252/373 |
| 5,472,986 | 12/1995 | Van Dijk . |

* cited by examiner

*Primary Examiner*—Johann Richter
*Assistant Examiner*—J. Parsa
(74) *Attorney, Agent, or Firm*—Pillsbury Winthrop LLP

(57) ABSTRACT

A process for the production of methanol comprises converting a hydrocarbon feedstock at a pressure above the desired synthesis pressure into a synthesis gas mixture containing hydrogen, carbon oxides and steam at an elevated temperature and pressure, cooling said mixture to condense water from the mixture, separating the condensed water, and passing the resultant gas mixture, with no further compression and no recycle of unreacted gas, at an elevated temperature through a series of at least two methanol synthesis stages with separation of synthesised methanol from the gas mixture after each stage is disclosed. The hydrocarbon feedstock is converted into the synthesis gas mixture by a catalytic steam reforming process wherein the heat required for reforming is supplied by the products of combustion of the unreacted gas remaining after separation of synthesised methanol, and, preferably also by the reformed gas after it has left the reforming catalyst.

4 Claims, 2 Drawing Sheets

PRODUCTION OF METHANOL

This is a continuation under 35 U.S.C. Section 120 of International application Ser. No. PCT/GB98/01670 filed on Jun. 8, 1998 which application designates the U.S.

This invention relates to methanol and in particular to the production thereof from a hydrocarbon feedstock.

Methanol is conventionally produced by subjecting a hydrocarbon feedstock to steam reforming, separation of the excess of steam, and then compression of the reformed gas to the desired synthesis pressure. The resultant synthesis gas, consisting of hydrogen, carbon oxides, methane and possibly a small proportion of nitrogen, is then added as "make-up gas" to a synthesis loop where it is mixed with recycled unreacted gas, heated to the desired synthesis inlet temperature and then passed over a synthesis catalyst. The effluent from the synthesis reactor is then cooled to condense methanol and the unreacted gas is recycled. A purge is generally taken from the loop to prevent a build-up of inerts.

The steam reforming step is conventionally effected by passing a hydrocarbon feedstock, in admixture with steam, at a pressure in the range 10–40 bar abs. over a catalyst, usually nickel on a support such as calcium aluminate cement or alumina, disposed in externally heated tubes. The tubes are heated such that the reformed gas leaves the catalyst at a temperature of the order of 700–900° C. The synthesis is generally effected at a pressure in the range 50–120 bar abs. The recycled unreacted gas typically forms 60–85% of the gas entering the synthesis reactor. A considerable amount of power is required to compress the make-up gas to the synthesis pressure and to recycle the unreacted gas, and also the compressor represents a considerable capital cost.

A methanol synthesis process with no compression of the synthesis gas after reforming has been proposed in U.S. Pat. No. 5,472,986. In this reference a hydrocarbon feedstock is compressed to a sufficiently high pressure prior to reforming by an adiabatic partial oxidation using enriched air. Instead of utilizing a synthesis loop, a plurality of synthesis stages is employed with separation of synthesized methanol after each synthesis stage: since the adiabatic partial oxidation process gives a hydrogen-deficient synthesis gas, hydrogen is recovered from the unreacted synthesis gas remaining after methanol synthesis and is recycled to the inlet of the first synthesis stage. However, since the recovered hydrogen is inevitably at a significantly lower pressure than the desired synthesis pressure, re-compression of the recovered hydrogen is necessary before recycle.

It has been proposed in U.S. Pat. No. 5,177,114 to employ a "single pressure" process where there is no compression of the gas after reforming and no recirculation of the unreacted gases. As in U.S. Pat. No. 5,472,986, the hydrocarbon feedstock is compressed to a sufficiently high pressure before reforming by adiabatic partial oxidation using air or enriched air and the synthesis gas is passed through a series of synthesis stages with separation of the synthesised methanol between the synthesis stages.

In the process of U.S. Pat. No. 5,177,114, there are typically two or three synthesis stages. After separation of the methanol from the last synthesis stage, the remaining gas is used to fuel a gas turbine driving the feedstock and air compressors. The carbon efficiency, i.e moles of methanol per gram atom of hydrocarbon carbon, of the process exemplified in this reference was said to be 60.5%, even though a high reforming pressure of 120 atmospheres was employed. Furthermore, since the methanol synthesis gas contains a relatively high proportion of inerts, mainly nitrogen resulting from the use of air or enriched air in the adiabatic partial oxidation step, a relatively large volume of methanol synthesis catalyst is required.

A "single-pressure" methanol synthesis process, utilizing a synthesis loop, is disclosed in U.S. Pat. No. 4,910,228 wherein the hydrocarbon feedstock is subjected to steam reforming in a heat-exchange reformer and the reformed gas is then subjected to partial oxidation with oxygen. The resultant hot partially oxidized reformed gas is then used to heat the heat exchange reformer. In this process, the heat exchange reformer is operated at such a pressure that the partially oxidized reformed gas was at a pressure equal to or above the inlet pressure of the loop circulator. The power requirements (to produce the compressed feedstock, oxygen, and circulation etc.) were supplied by combustion of part of the loop purge and by steam raised in the methanol synthesis stage.

We have now devised a "single-pressure" process using a heat exchange reformer that does not require a hydrogen recovery, air enrichment, or oxygen production unit. In the process of the present invention, the synthesis gas is produced by steam reforming in a pressurized heat exchange reformer wherein heat for reforming is supplied to the gas undergoing reforming from a) the products of combusting a fuel comprising the unreacted synthesis gas remaining after the series of synthesis stages, and preferably also b) from the reformed gas. The heat exchange reformer is preferably a modification of the type described in the aforesaid U.S. Pat. No. 4,910,228.

Accordingly the present invention provides a process for the production of methanol comprising converting a hydrocarbon feedstock at a pressure above the desired synthesis pressure into a synthesis gas mixture containing hydrogen, carbon oxides and steam at an elevated temperature and pressure, cooling said mixture to condense water from the mixture, separating the condensed water, and passing the resultant gas mixture, with no further compression and no recycle of unreacted gas, at an elevated temperature through a series of at least two methanol synthesis stages with separation of synthesized methanol from the gas mixture after each stage, and combusting the remaining unreacted gas with compressed air, wherein the hydrocarbon feedstock is converted into said synthesis gas mixture by passing a mixture of said hydrocarbon feedstock and steam through a steam reforming catalyst disposed in reformer tubes heated by the products of the combustion of said unreacted gas and, preferably, also by the reformed gas after it has left the reforming catalyst.

In one type of heat exchange reformer, the catalyst is disposed in tubes extending between a pair of tube sheets through a heat exchange zone. Reactants are fed to a zone above the upper tube sheet and pass through the tubes and into a zone beneath the lower tube sheet. The heating medium is passed through the zone between the two tube sheets. A heat exchange reformer of this type is described in GB 1 578 270.

In order to obtain a reformed gas with a reasonably low methane content, it is necessary that the reformed gas leaves the catalyst at a relatively high temperature, for example in the range 850–1100° C. For efficient operation, heat has to be recovered from this high temperature reformed gas. While, when using a heat exchange reformer of the type described in the aforementioned GB 1 578 270, heat can be recovered from the hot reformed gas by steam raising, reactants pre-heating etc., in the present invention it is preferred to use at least some of this high grade heat to supply part of the heat required for the endothermic reforming reaction. Thus by employing a different type of heat exchange reformer and effecting heat exchange between the reformed gas and the gas undergoing reforming as it passes through the catalyst, high grade heat in the reformed gas can be recovered directly as part of the heat required for the endothermic reforming process and the reformed gas can be partially cooled. Hence it is preferred to employ a heat exchange reformer wherein heat is supplied to the catalyst from the products of combustion of the unreacted gas remaining after methanol synthesis and from the reformed gas that has left the catalyst.

The preferred type of heat exchange reformer is a double-tube heat exchange reformer wherein the reformer tubes each comprise an outer tube having a closed end and an inner tube disposed concentrically within the outer tube and communicating with the annular space between the inner and outer tubes at the closed end of the outer tube with the steam reforming catalyst disposed in said annular space. The mixture of hydrocarbon feedstock and steam is fed to the end of the outer tubes remote from said closed end and the external surface of the outer tubes is heated by the products of the combustion of said unreacted gas so that the mixture passes through said annular space and undergoes steam reforming and then passes through the inner tube. Unlike the double-tube reformer of the aforesaid U.S. Pat. No. 4,910,228, in the present invention no insulation is provided on the walls of the inner tube. Consequently, as the reformed gas passes through the inner tube, heat is transferred from the reformed gas through the wall of the inner tube into the annular space and so augments the heat supplied from the combustion products of the unreacted gas. In this way also the reformed gas is cooled and so less heat has to be recovered from the reformed gas.

In the process of the invention the feedstock may be any gaseous or low boiling hydrocarbon feedstock such as natural gas or naphtha. It is preferably methane or natural gas containing a substantial proportion, e.g. over 90% v/v methane. If the feedstock contains sulphur compounds, before, or preferably after, compression the feedstock is subjected to desulphurization, e.g. hydrodesulphurization and absorption of hydrogen sulphide using a suitable absorbent, e.g. a zinc oxide bed. Usually it is desirable to incorporate a hydrogen-containing gas into the feedstock prior to hydrosulphurization: a part of the residual unreacted synthesis gas can be used as the hydrogen-containing gas. The feedstock is preferably compressed to a pressure in the range 40–100 bar abs.

Before, or preferably after, compression of the feedstock, steam is mixed with the feedstock: this steam introduction may be effected by direct injection of steam and/or by saturation of the feedstock by contact of the latter with a stream of heated water. The amount of steam introduced is preferably such as to give a steam ratio of 1.4 to 3.0, i.e. 1.4 to 3.0 moles of steam per gram atom of carbon in the feedstock. The amount of steam is preferably minimized as this leads to a more efficient process. It is preferred that the steam ratio is below 2.7.

The resultant steam/feedstock mixture is then subjected to reforming. Before it is fed to the heat exchange reformer, the feedstock/steam mixture may be subjected to a step of adiabatic low temperature reforming. In such a process, the hydrocarbon steam mixture is heated, typically to a temperature in the range 400–600° C., and then passed adiabatically through a bed of a suitable catalyst, usually a catalyst having a high nickel content, for example above 40% by weight. During such an adiabatic low temperature reforming step any hydrocarbons higher than methane react with steam to give a mixture of methane, carbon oxides and hydrogen. The use of such an adiabatic reforming step, commonly termed pre-reforming, is desirable to ensure that the feed to the heat exchange reformer contains no hydrocarbons higher than methane and also contains a significant amount of hydrogen. This is desirable in order to minimise the risk of carbon formation on the catalyst in the heat-exchange reformer.

After any such pre-reforming step, the feedstock/steam mixture is further heated, if necessary, to the heat exchange reformer inlet temperature which is typically in the range 450–600° C. During passage through the reforming catalyst, which is usually nickel supported on a refractory support such as rings or pellets of calcium aluminate cement, alumina, titania, zirconia and the like, the endothermic reforming reaction takes place with the heat required for the reaction being supplied from the products of combustion of the unreacted synthesis gas flowing past the exterior surface of the outer tubes, and, if the preferred form of heat exchange reformer is employed, also from the reformed gas after it has left the catalyst. The temperature of the combusted unreacted synthesis gas is preferably sufficient that the gas undergoing reforming in the annular space leaves the catalyst at to a temperature in the range 800–1200° C. For a given feedstock/steam mixture and reforming pressure, this temperature largely determines the composition of the reformed gas. From the viewpoint of process efficiency, the greater the temperature the better, but metallurgical problems increase as the temperature is increased. For this reason the temperature at which the reformed gas leaves the catalyst is preferably in the range 900–1100° C. The maximum temperature that can be tolerated also depends upon the pressure differential between the gas undergoing reforming and the heating gas, i.e. the product of combusting the unreacted gas remaining after methanol synthesis. It is preferred that the latter is at a pressure no more than 20 bar below the pressure of the gas undergoing reforming.

As indicated above, when using the preferred form of heat exchange reformer, during passage through the inner tubes, the reformed gas cools by transferring heat to the gas undergoing reforming in the annular space. Preferably the gas cools by several hundred ° C. but of course it will leave the inner tubes at a temperature somewhat above the temperature at which the feedstock/steam mixture is fed to the heat exchange reformer. Preferably, when using the preferred type of heat exchange reformer, the reformed gas leaves the inner tubes at a temperature in the range 600–850° C.

The reformed gas leaving the heat exchange reformer is then cooled with heat recovery, e.g. by steam raising and/or boiler feedwater heating, feedstock preheating etc., and then with cooling water to condense the residual steam as water. The water is then separated and the resultant synthesis gas is passed, without any further compression, to the first methanol synthesis stage.

During passage of the feedstock/steam mixture through the heat exchange reformer (and any pre-reformer), and of the reformed gas through the heat recovery stages, it will encounter some drop in pressure. Typically the pressure drop will be of the order of 3–8 bar. Hence the pressure to which the feedstock is initially compressed should be sufficiently above the desired inlet pressure for the first synthesis reactor to compensate for this inevitable pressure drop.

Each methanol synthesis stage has one or more stages of heat exchange to heat the synthesis gas to the desired synthesis inlet temperature. While the heat source may be any suitable heat source, for example one of the heat recovery stages employed to cool the reformed gas, it is preferred that the heat source for at least part of the heating is the reacted synthesis gas leaving the synthesis reactor of that stage, i.e. there is a feed/effluent heat exchanger.

After heating to the desired synthesis inlet temperature, the synthesis gas is passed to the synthesis reactor where it contacts the methanol synthesis catalyst. This is preferably shaped particles, e.g. pellets of a copper catalyst obtained by reduction of a precursor consisting of copper oxide and one or more supporting components such as chromia, magnesia, zinc oxide or alumina. Preferred precursors are those obtained by calcination of a co-precipitated mixture of copper, zinc, aluminium, and optionally also magnesium compounds. The methanol synthesis reaction is exothermic and the equilibrium is favored towards methanol synthesis by low temperatures. However the catalytic activity increases as the temperature is increased. It is preferred to effect the synthesis reaction with a reactor outlet temperature in the range 200–260° C., preferably below 250° C., at least in the second and any subsequent synthesis stages.

It is preferred that the synthesis reactor for at least the first methanol synthesis stage is of the "quasi isothermal" type wherein the catalyst temperature is maintained essentially constant by heat exchange means in the reactor whereby heat evolved by the synthesis reaction is transferred to a coolant, which is preferably boiling water. The coolant may circulate through tubes extending through the catalyst bed. An example of this type of reactor is described in EP 0 081 948. Alternatively, but less preferably, the catalyst may be disposed in tubes and the coolant circulated around the exterior of the tubes. Where the coolant is boiling water, the resultant steam may be used for supplying heat for distillation of the crude methanol and/or may be let down in a turbine to supplement the power required for feedstock and/or air compression. Alternatively, and particularly for the second and any subsequent synthesis stage, a reactor of the type disclosed in U.S. Pat. No. 4,778,662 where the catalyst bed is cooled by heat exchange with the incoming synthesis gas may be employed but in this case it is preferred, unlike the reactor described in that reference, that there is little or no adiabatic bed below the cooling tubes. An alternative type of reactor, again particularly for the second and any subsequent reactor, is a reactor of the so-called "quench" type. In this type of reactor the catalyst is disposed as multiple beds and part of the synthesis gas is fed to the first bed and part is injected as "quench" gas into the reactor between beds. Alternatively a single bed "quench" reactor may be employed wherein the catalyst is disposed as a single bed and part of the synthesis gas is fed to the bed inlet and part is injected as "quench" gas part way through the bed. In either single or multiple bed quench reactors there may be multiple injections of the quench gas.

After synthesis, the reacted gas is cooled, for example by feed/effluent heat exchange as aforesaid, and then by heat exchange with a suitable coolant to condense methanol as a liquid. The condensed methanol is then separated, and the unreacted gas passed to the next synthesis stage. In some cases it may be desirable to effect the cooling by direct injection of cold water. However this method has the disadvantage that the duty of any subsequent methanol distillation stage is increased.

As indicated above there may be two or more stages of methanol synthesis. It is preferred that there are three stages. Since the synthesis gas will experience a pressure drop as it passes through each synthesis stage, the synthesis pressure in the synthesis stages will progressively decrease. However, the pressure drop is relatively small and will normally be no more than about 2 bar abs. in each stage. After the separation of synthesized methanol in the last synthesis stage, part of the remaining unreacted synthesis gas may be recycled to the feedstock to provide the hydrogen-containing gas required for hydrodesulphurizing while the remainder is combusted with compressed air and the combustion products are used to heat the heat exchange reformer. As a result of the pressure drop encountered during the reforming and synthesis stages, the remaining unreacted synthesis gas will have a pressure somewhat below that of the pressure of the compressed feedstock fed to the heat exchange reformer. However, apart from that portion, if any, that is recycled to provide the hydrogen-containing gas for addition to the feedstock prior to hydrodesulphurization, there is generally no need to compress the unreacted synthesis gas prior to combustion.

As indicated above, the unreacted synthesis gas is used as fuel to heat the heat exchange reformer: in some cases it may be necessary to supplement the unreacted synthesis gas with another fuel supply, for example part of the feedstock. Alternatively, where there is sufficient unreacted synthesis gas, the latter may also be used as fuel for other purposes, e.g. to pre-heat reactants, raise steam and/or fuel a gas turbine driving the feedstock compressor and the compressor required to provide the compressed air for combustion of the unreacted synthesis gas.

BRIEF DESCRIPTION OF THE DRAWINGS

One embodiment of the invention is illustrated by reference to the accompanying drawings wherein

Referring to FIG. 1, a feedstock such as natural gas is fed via line 10 at the supply pressure, which is typically about 35 bar abs., to a compressor 11 where it is compressed to a pressure about 6–10 bar above the desired synthesis pressure, for example to 85 bar abs. If the feed is free from hydrogen, a small proportion of a hydrogen-containing gas is fed to the final stage of the compressor via line 12. The compressed gas is then fed, via line 13, to a heat exchanger 14 wherein it is heated, typically to a temperature in the range 200 to 300° C., and then fed to a vessel 15 containing a bed of a hydrodesulphurization catalyst, for example cobalt molybdate, and a bed of an absorbent, such as zinc oxide, for hydrogen sulphide. Any sulphur compounds present in the feed are converted to hydrogen sulphide by the hydrodesulphurization catalyst and the resultant hydrogen sulphide is absorbed by the absorbent.

Steam is then added to the desulphurized gas via line 16. The amount of steam added is typically 1.4 to 3 moles for every gram atom of hydrocarbon carbon in the feedstock. Instead of direct addition of steam, steam can be introduced by saturation wherein the heated desulphurized feedstock is contacted with a stream of hot water.

The resultant desulphurized feedstock/steam mixture is then heated to a temperature typically in the range 450–600° C. in heat exchanger 17 and fed to an adiabatic pre-reformer 18 containing a bed of a suitable low temperature reforming catalyst, for example a high nickel content catalyst obtained by co-precipitating nickel and aluminium compounds followed by calcination and reduction. During passage through the pre-reformer 18, some steam reforming takes place and any higher hydrocarbons in the feedstock are decomposed, to give a pre-reformed gas comprising methane, hydrogen, carbon oxides and unreacted steam. The temperature at which the pre-reformed gas leaves the pre-reformer 18 will depend on the proportion of higher hydrocarbons in the feedstock: thus if there are sufficient higher hydrocarbons, the net reaction in pre-reformer 18 may be exothermic and so the exit temperature will be greater than the feed temperature. However, generally the reaction in pre-reformer 18 will be net endothermic.

Figure 1:
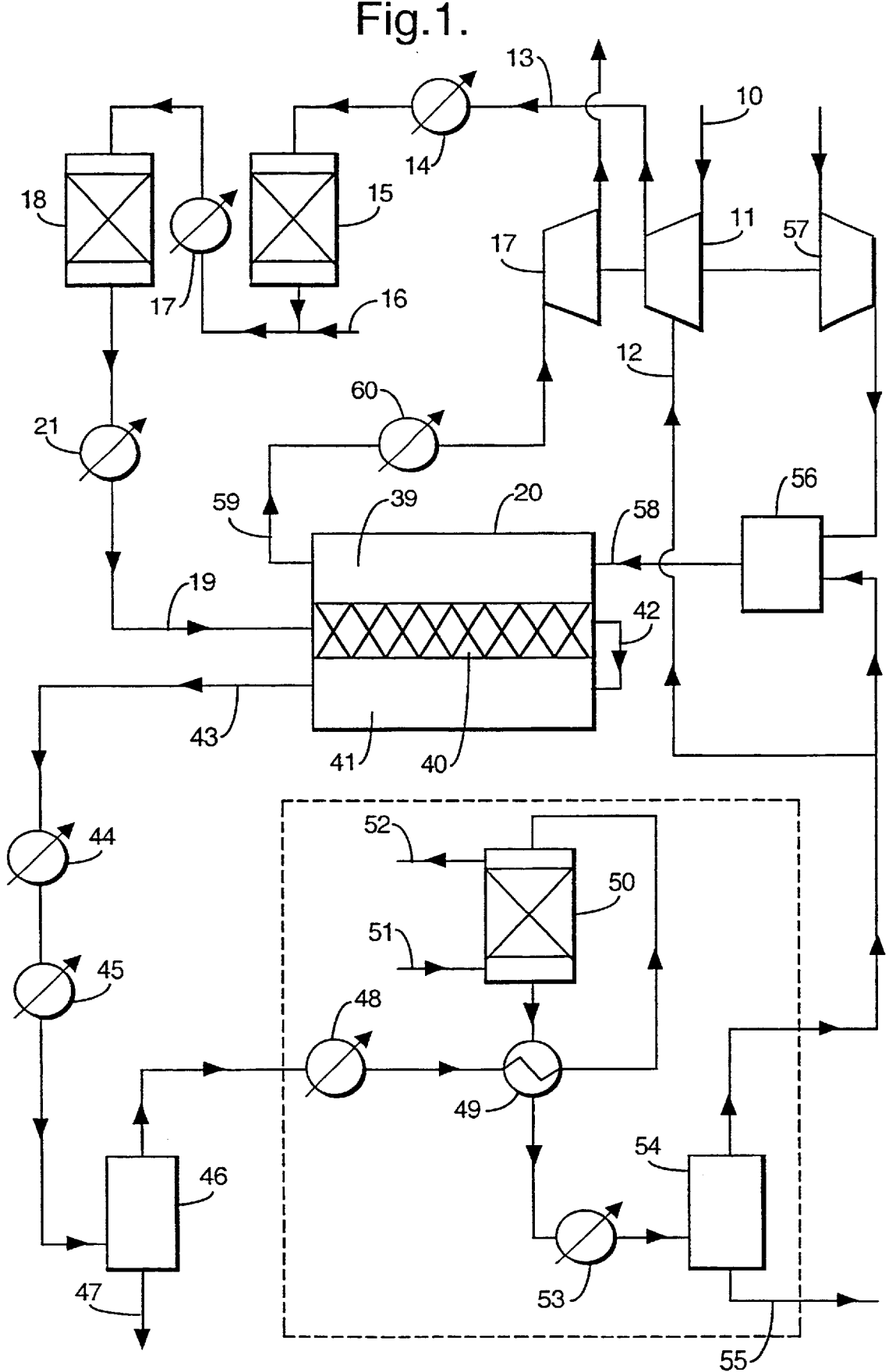
FIG. 1 is a diagrammatic flowsheet of a process in accordance with the invention

The pre-reformed gas is then fed, via line 19, to a heat exchange reformer 20 which is shown diagrammatically in FIG. 1. Desirably the inlet temperature to the heat exchange reformer is in the range 400–600° C. and so, if necessary, the pre-reformed gas is heated to the desired inlet temperature in heat exchanger 21 prior to feeding to the heat exchange reformer 20.

Figure 2:
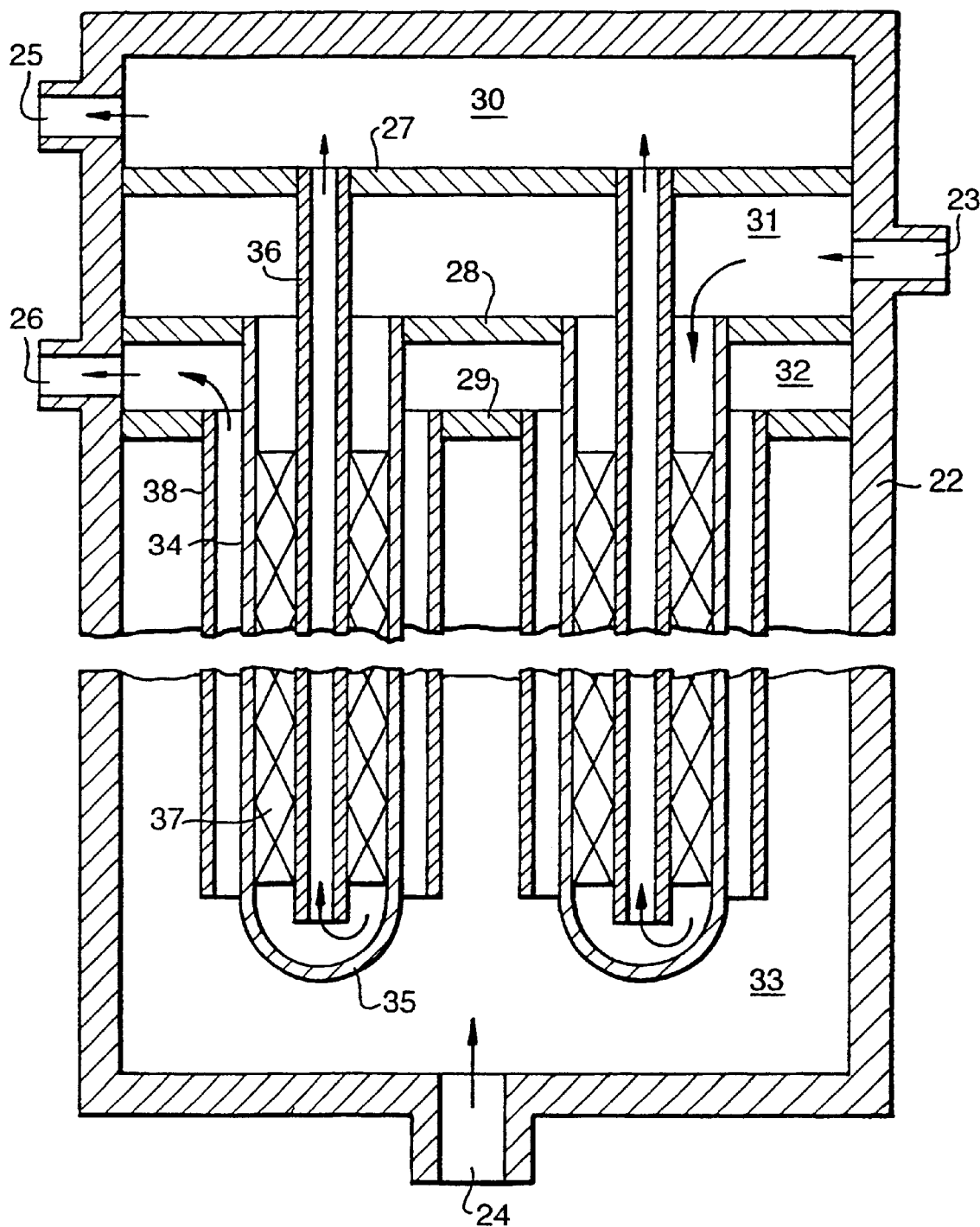
FIG. 2 is a diagrammatic section of a double tube reformer for use in the process of FIG. 1.

The heat exchange reformer 20 is preferably of the type shown in FIG. 2. In this figure, for simplicity, only two sets of reforming tubes are shown: it will be appreciated that there may be several tens or even hundreds of sets of tubes. The reformer has an outer pressure shell 22 provided with two inlet ports 23, 24 and two outlet ports 25, 26. Disposed across the shell 22 are three tubesheets 27, 28, 29 dividing the space within the shell into a number of separate zones with each of which one of the ports communicates. The upper tubesheet 27 defines, with the top and walls of the shell 22, a reformed gas off-take zone 30 with which outlet port 25 communicates. The intermediate tubesheet 28 defines, with the walls of the shell and the upper tube plate 27, a reactants feed zone 31 with which the reactants feed port 23 communicates. The lower tubesheet 29 defines, with the walls of the shell 22 and the intermediate tubesheet 28, a combustion gas outlet zone 32 with which outlet port 26 communicates, and also defines, with the walls and bottom of shell 22, a heat exchange zone 33 which extends for most of the length of the reformer and with which the combustion gas inlet port 24 communicates. Extending from the intermediate tubesheet 28 through tubesheet 29 and into the heat exchange zone 33 for most of the length of the latter are a plurality of outer tubes 34, closed at their lower ends 35. Extending from tubesheet 27 through tubesheet 28 and into the outer tubes 34 are a plurality of inner tubes 36, one for each outer tube 34. Tubes 36 are open at their lower ends and terminate close to the closed end of the outer tubes 34. A bed 37 of a particulate steam reforming catalyst, typically nickel supported on calcium aluminate cement rings, is disposed in the annular space between each outer tube 34 and its associated inner tube 36. The catalysts particles, e.g. rings, are supported within the annular space by means of a perforate plate or mesh (not shown) at the lower end of the outer tubes. Disposed round each outer tube 34 is a sheath 38 supported by the lower tubesheet 29.

In operation, hot gas is fed to the combustion gas inlet port 24. This hot gas passes up the annular space between each sheath 38 and the outer surface of its associated outer tube 34, thereby transferring heat through the wall of the outer tube 34 into the catalyst filled annular space between the outer and inner tubes. From the top of sheaths 38, the hot gas, now cooled as a result of the heat exchange transferring heat into the catalyst bed 37, passes into the combustion gas off-take zone 32 and leaves the reformer shell via port 26. The feedstock/steam mixture, i.e. the pre-reformed gas, is fed, via line 19 (as shown in FIG. 1), to the reactants feed port 23 from whence it flows through the reactants feed zone 31 into the annular space within each outer tube 34. The pre-reformed gas thus contacts the steam reforming catalyst 37 in the annular space and undergoes the steam reforming reaction with the heat required for the endothermic reforming reaction being provided mainly by the heat transferred from the hot gas passing up through the annular space between the sheathes 38 and the outer tube 34. At the lower end 35 of the outer tubes 34, the reformed gas leaves the catalyst and passes up through the inner tubes 36, transferring heat back into the catalyst bed to supply the remainder of the heat required for the reforming reaction. The reformed gas leaves the upper end of the inner tubes 36 and passes through the reformed gas off-take zone 30 and leaves the reformer via port 25. Typically the temperature of the pre-reformed gas fed to inlet port 23, is of the order of 400 to 600° C., and the temperature of the reformed gas leaving the catalyst, i.e. at the lower end of the outer tubes 34, is of the order of 850 to 1100° C. The temperature of the hot combustion gas supplied to the combustion gas inlet port 24 has a temperature above, typically 50 to 300° C. above, the temperature of the reformed gas leaving the catalyst, i.e. at the lower end of the outer tubes 34, and so is generally in the range 1000–1400° C. As a result of the heat exchange the hot gas leaving the combustion gas outlet port 26 generally has a temperature about 50 to 200° C. above the reactants inlet temperature, while during passage through the inner tubes, the reformed gas cools to a temperature that is typically about 50 to 300° C. above the reactants feed temperature.

Reverting to FIG. 1, the heat exchange reformer 20 is shown diagrammatically. The upper zone 39 corresponds to the heat exchange zone 33 of FIG. 2 and in particular to the annular space between the sheathes 38 and the outer tubes 34. The centre zone 40 corresponds to the catalyst-containing zone of FIG. 2, i.e. the annular space between the outer tubes 34 and the associated inner tubes 36, while the lower zone 41 corresponds to the region within the inner tubes 36 of FIG. 2. Line 42 represents the connection, at the lower end of the outer tubes 34, between the outlet of the catalyst-containing zone and the interior of tubes 36 of FIG. 2. The reformed gas leaves the heat exchange reformer via line 43 from port 25 of FIG. 2.

It will be appreciated that if the less preferred type of reformer is employed, for example a heat exchange reformer of the type described in GB 1 578 270, wherein heat is not directly recovered from the reformed gas leaving the catalyst and used to supply heat for reforming, reformed gas passes directly from the catalyst bed zone 40 to line 43 without passing through line 42 and zone 41.

The reformed gas is fed via line 43 to a heat exchanger 44 wherein it is cooled, with heat recovery, and then further cooled with cooling water in heat exchanger 45 to condense the excess of steam in the reformed gas as water. The condensed water is then separated in separator 46 and removed via line 47. It will be appreciated that heat exchanger 44 may comprise a series of heat exchangers performing different heat recovery duties, such as steam raising, reactants pre-heating, boiler feed water heating, distillation heating etc.

The dewatered synthesis gas is taken from separator 46 and heated in heat exchanger 48 and feed/effluent heat exchanger 49, typically to about 200 to 260° C., and fed to a methanol synthesis reactor 50. This reactor has a bed of a copper-based methanol synthesis catalyst in which are disposed cooling tubes through which a coolant, e.g. water boiling at elevated pressure, is circulating. The coolant is fed to the synthesis reactor via line 51 and leaves via line 52. The reacted synthesis gas is then fed from reactor 50 to feed/effluent heat exchanger 49 wherein it cools by heat transfer to the synthesis reactor feed and then it is further cooled in heat exchanger 53 to condense the synthesized methanol which is separated in separator 54 giving a crude methanol product which is collected via line 55.

The methanol synthesis stage within the dotted line is repeated one or more times. The crude methanol separated in each synthesis stage may be combined and fed to a distillation stage (not shown). The number of methanol synthesis stages employed will depend upon economic considerations. Thus depending on the reforming and synthesis conditions employed, the amount of methanol that could be produced in a third, or subsequent, stage may be insufficient to justify the expense of the additional methanol synthesis reactor, heat exchangers and separator.

The methanol synthesis stages may be similar to one another but may be operated at different temperatures, which may be controlled by control of the pressure of the coolant supplied to the cooling tubes of the synthesis reactors. While it is preferred that the first methanol synthesis stage employs a reactor having a circulating coolant, in some cases it may be preferable to employ an alternative type of synthesis reactor for the second and any subsequent stages. For example there may be used a reactor of the type described in U.S. Pat. No. 4,778,662 wherein the coolant is the feed being heated to the synthesis inlet temperature. Thus when using this type of reactor, the feed/effluent heat exchanger 49 may be omitted.

After separation of the condensed methanol from the last synthesis stage, part of the remaining unreacted gas is fed, if required, via line 12 to the feedstock compressor 11 as the hydrogen-containing gas required for hydrodesulphurization. The remainder is fed as fuel to a combustor 56 where the remainder of the unreacted synthesis gas is combusted with compressed air supplied from a compressor 57. The air compressor will normally be of the multi-stage type with inter-stage cooling. Heat can be recovered in such inter-stage cooling and used, e.g. for boiler feedwater heating. Such heat recovery is however not shown in FIG. 1. The hot combustion products are then fed, via line 58, as the hot gas to port 24 of the heat exchange reformer 20.

The partly cooled combustion products leaving outlet port 26 of the heat exchange reformer 20 are fed via line 59 to heat exchanger 60 wherein heat is recovered, and then power is recovered by letting down the combustion products in a turbine 61. It will be appreciated that heat exchanger 60 may comprise a series of heat exchangers performing different heat recovery duties, such as steam raising, reactants pre-heating, boiler feed water heating, distillation heating etc.

Turbine 61 is used to drive compressors 11 and 57. Alternatively, or additionally, the compressors 11 and 57 may be powered by steam raised from the synthesis stages and/or from heat recovery in heat exchangers 44 and/or 60. The process steam (or hot water used for saturating the desulphurized feedstock) may be raised from heat recovered in heat exchangers 44 and 60.

In addition to providing the heat required for raising the process steam, for heat exchangers 14, 17, 21 (if used), and 48, and also for distillation of the crude methanol, sufficient heat and power is generally available from turbine 61, the heat recoveries in heat exchangers 44 and 60, together with heat recovered from air compression interstage cooling and the coolant used in the synthesis stages, to supply the compression power requirements without the need for supplementary fuel to be burnt. However, in some cases it may be desirable to feed some of the compressed feedstock to the combustor 56.

The invention is illustrated by the following calculated example of a plant producing about 1540 te/day of methanol in the crude product from natural gas (methane 92.2%, ethane 3.1%, propane 0.4%, butanes 0.1%, carbon dioxide 0.5%, nitrogen 21%, hydrogen 1.5% by volume) supplied at a pressure of 35 bar abs. using the flowsheet of FIG. 1 and a heat exchange reformer of the type shown in FIG. 2. Since the natural gas contained some hydrogen, there was no need to recirculate some of the unreacted gas via line 12. Heat exchanger 21 was omitted, i.e. the pre-reformed gas was fed directly to the heat exchange reformer without further heating. Three methanol synthesis stages (designated by the suffixes "a" "b" and "c") were employed.

The temperature T, pressure P (in bar abs.) and flow rates (rounded to the nearest integer) of the various streams are shown in the Table 1.

The overall carbon efficiency (methanol in crude product/feedstock hydrocarbon carbon) of the process is 64.2% while the synthesis carbon efficiency (methanol in crude product/carbon oxides in synthesis gas fed to first stage) is 86.9%. Calculation shows that the volumes of catalyst (after reduction) required for the three methanol synthesis stages are respectively 45 m$^3$, 30 m$^3$ and 20 m$^3$, i.e. a total of 95 m$^3$, assuming conventional commercially available methanol synthesis catalysts are employed.

TABLE 1

| Stream | T(° C.) | P | Flow rate (kmol/h) | | | | | | |
|---|---|---|---|---|---|---|---|---|---|
| | | | $CH_4$ | CO | $CO_2$ | $H_2$ | $N_2$ + Ar | $CH_3OH$ | $H_2O$ |
| natural gas feed 10 | 20 | 35 | 3125* | 0 | 16 | 47 | 69 | 0 | 0 |
| steam 16 | 303 | 85 | 0 | 0 | 0 | 0 | 0 | 0 | 6250 |
| pre-reformer 18 feed | 550 | 83 | 3125* | 0 | 16 | 47 | 69 | 0 | 6250 |
| pre-reformer 18 product | 510 | 83 | 2901 | 7 | 232 | 804 | 69 | 0 | 5810 |
| ex reforming catalyst 37 | 1000 | 80 | 832 | 1821 | 488 | 7268 | 69 | 0 | 3484 |
| reformed gas 43 | 800 | 80 | 832 | 1821 | 488 | 7268 | 69 | 0 | 3484 |
| gas ex separator 46 | 40 | 79 | 832 | 1821 | 487 | 7268 | 69 | 0 | 14 |
| reactor 50a in | 220 | 79 | 832 | 1821 | 487 | 7268 | 69 | 0 | 14 |
| reactor 50a out | 242 | 78 | 832 | 555 | 447 | 4616 | 69 | 1306 | 54 |
| crude product 55a | 40 | 78 | 11 | 3 | 28 | 6 | 0 | 1263 | 54 |
| reactor 50b in | 220 | 78 | 821 | 552 | 419 | 4610 | 68 | 43 | 1 |
| reactor 50b out | 235 | 77 | 821 | 138 | 320 | 3485 | 68 | 556 | 100 |
| crude product 55b | 40 | 77 | 6 | 0 | 12 | 2 | 0 | 528 | 98 |
| reactor 50c in | 220 | 77 | 815 | 138 | 308 | 3483 | 68 | 29 | 2 |
| reactor 50c out | 224 | 76 | 815 | 51 | 188 | 2948 | 68 | 236 | 122 |
| crude product 55c | 40 | 76 | 2 | 0 | 4 | 1 | 0 | 216 | 119 |
| total crude product | 40 | 76 | 19 | 4 | 43 | 8 | 1 | 2007 | 271 |
| gas ex separator 54c | 40 | 76 | 813 | 51 | 184 | 2948 | 68 | 19 | 3 |

TABLE 1-continued

| Stream | T(° C.) | P | Flow rate (kmol/h) | | | | | | |
| --- | --- | --- | --- | --- | --- | --- | --- | --- | --- |
| | | | $CH_4$ | CO | $CO_2$ | $H_2$ | $N_2$ + Ar | $CH_3OH$ | $H_2O$ |
| air to combustor 56** | 363 | 77 | 0 | 0 | 16 | 0 | 40982 | 0 | 0 |
| combusted gas 58*** | 1092 | 76 | 0 | 0 | 1083 | 0 | 41050 | 0 | 4615 |
| combusted gas 69*** | 778 | 75 | 0 | 0 | 1083 | 0 | 41050 | 0 | 4615 |

*of which 2881 kmol/h is methane and 244 kmol/h is higher hydrocarbons expressed as $CH_{2.923}$
**contains 10898 kmol/h of oxygen in addition to listed components
***contains 7744 kmol/h of oxygen in addition to listed components.

What is claimed is:

1. A process for the production of methanol comprising converting a hydrocarbon feedstock into a synthesis gas mixture containing hydrogen, carbon oxides and steam at an elevated temperature and pressure, cooling said mixture to condense water from the mixture, separating the condensed water, and passing the resultant gas mixture, with no further compression and no recycle of unreacted gas, at an elevated temperature through a series of at least two methanol synthesis stages with separation of synthesized methanol from the gas mixture after each stage, and combusting at least part of the remaining unreacted gas with compressed air, wherein the hydrocarbon feedstock is converted into said synthesis gas mixture by passing a mixture of said hydrocarbon feedstock and steam through a steam reforming catalyst disposed in reformer tubes heated by the products of the combustion of said unreacted gas.

2. A process according to claim 1 wherein said reformer tubes are heated by the reformed gas after it has left the reforming catalyst in addition to being heated by the products of the combustion of said unreacted gas.

3. A process according to claim 2 wherein the reformer tubes each comprise an outer tube having a closed end and an inner tube disposed concentrically within the outer tube and communicating with the annular space between the inner and outer tubes at the closed end of the outer tube with the steam reforming catalyst disposed in said annular space and the mixture of hydrocarbon feedstock and steam is fed to the end of the outer tubes remote from said closed end and the external surface of the outer tubes is heated by the products of the combustion of said unreacted gas whereby the mixture passes through said annular space and undergoes steam reforming to form a reformed gas which then passes through the inner tube with transfer of heat from the reformed gas through the wall of the inner tube into the annular space and thus augmenting the heat supplied from the combustion products of the unreacted gas.

4. A process according to claim 1 wherein there are three methanol synthesis stages.

* * * * *